United States Patent [19]

Malguzzi et al.

[11] Patent Number: 5,258,531

[45] Date of Patent: Nov. 2, 1993

[54] PROCESS FOR THE DIRECT SYNTHESIS OF ORGANOTIN COMPOUNDS AND THEIR USE

[75] Inventors: Romualdo Malguzzi, Lodi; Maurizio Sandri, Milan, both of Italy; Michael Rosenthal; Albert W. Puerzer, both of München, Fed. Rep. of Germany

[73] Assignee: Baerlocher GmbH, Munich, Fed. Rep. of Germany

[21] Appl. No.: 860,507

[22] PCT Filed: Dec. 17, 1990

[86] PCT No.: PCT/EP90/02219

§ 371 Date: Jun. 17, 1992

§ 102(e) Date: Jun. 17, 1992

[87] PCT Pub. No.: WO91/09039

PCT Pub. Date: Jun. 27, 1991

[30] Foreign Application Priority Data

Dec. 18, 1989 [DE] Fed. Rep. of Germany ..... 89123402

[51] Int. Cl.$^5$ ............................................. C07F 7/22
[52] U.S. Cl. ...................................... 556/87; 556/98
[58] Field of Search ................................. 556/98, 87

[56] References Cited

U.S. PATENT DOCUMENTS

| | | | |
|---|---|---|---|
| 2,852,543 | 9/1958 | Blitzer et al. | 260/429.7 |
| 3,466,311 | 9/1969 | Mizuno et al. | 260/429.7 |
| 3,519,665 | 7/1970 | Molt et al. | 260/429.7 |
| 3,745,183 | 7/1973 | Katsumura et al. | 260/429.7 |
| 3,857,868 | 12/1974 | Witman et al. | 260/429.7 |
| 4,052,427 | 10/1977 | Leistner et al. | 260/429.7 |
| 4,128,565 | 12/1978 | Yajima et al. | 260/429.7 |
| 4,510,095 | 4/1985 | Holland et al. | 260/429.7 |

FOREIGN PATENT DOCUMENTS

0018327 10/1980 European Pat. Off. .
0032106 7/1981 European Pat. Off. .
0081458 4/1984 European Pat. Off. .
1168456 10/1969 United Kingdom ............. 556/98

OTHER PUBLICATIONS

G. W. Becker et al.: "Kunststoff Handbuch, 2/1, Polyvinylchlorid", 1985, Hanser, (Munich, Germany) pp. 527–431.

Primary Examiner—José G. Dees
Assistant Examiner—Porfirio Nazario-Gonzalez
Attorney, Agent, or Firm—Browdy and Neimark

[57] ABSTRACT

The invention relates to a process for the direct synthesis of organotin compounds of the formula $$R_n SnCl_{4-n}$$

wherein
n=1-4, and,
R=a linear or branched or cycloaliphatic alkyl having 4-18 C atoms, by reacting metallic tin with alkyl chlorides, characterized in that the reaction is carried out in the presence of amines of the general formula A) $R^1{}_a N[(CH_2CH_2O)_m CH_2CH_2OR^2]_{3-a}$ and/or ammonium chlorides of the formula B) $R^1{}_b N[(CH_2CH_2O)_m CH_2CH_2OR^2]_{4-b} Cl$ wherein
a=0, 1 or 2;
b=0, 1, 2 or 3;
$R^1$ = linear or branched or cycloaliphatic alkyl having 2 to 24 C atoms, aryl, alkyl aryl or substituted aryl and, if a=2, or b=2 or 3, the $R^1$ groups may be the same or different;
$R^2$ = H, linear or branched alkyl having 1 to 20 C. atoms, aryl, substituted aryl or alkyl aryl; and
m=1-20.

8 Claims, No Drawings

PROCESS FOR THE DIRECT SYNTHESIS OF ORGANOTIN COMPOUNDS AND THEIR USE

DESCRIPTION

The present invention relates to a process for the direct synthesis of organotin compounds of the general formula $$R_nSnCl_{4-n} \quad (1)$$

wherein n=1-4, and,

R=linear or branched or cycloaliphatic alkyl having 4 to 18 C atoms including mixtures of such compounds and their use.

The synthesis of organotin compounds, in particular organotin chlorides of the above-mentioned formula (1) is customarily predominantly carried out industrially according to the following methods:

reaction of tin tetrachloride with aluminum alkylene Grignard synthesis

In the direct synthesis from tin metal according to the reaction equation (2) indicated in the following the balance is on the left side, and any significant yields of desired compounds cannot be obtained without suited catalysts.

$$Sn + 2R'Cl \rightleftharpoons R'_2SnCl_2, (R'=alkyl) \quad (2)$$

The alkyl tin chlorides lead to the following secondary reactions with alkyl chlorides and/or tin metal:

(a) $R'_2SnCl_2 + Sn + R'Cl \rightarrow R'_3SnCl + SnCl_2$
(b) $R'_2SnCl_2 + Sn + 2 R'Cl \rightarrow R'_4Sn + 2SnCl_2$
(c) $4R'_3SnCl + Sn \rightarrow 3R'_4Sn + 2SnCl_2$ Moreover, autocomproportioning reactions are also possible:

$$R'_3SnCl + R'SnCl_3 \rightarrow 2R'_2SnCl_2 \quad (3)$$

and also the formation of by-products, in particular from $SnCl_2$:

$$SnCl_2 + R'Cl \rightarrow R'SnCl_3 \quad (4)$$

Thus the following compounds:

$$R'_4Sn, R_3'SnCl, R'SnCl_2, R'SnCl_3 \text{ and } SnCl_2$$

may be present in the reaction mixture in the synthesis described above.

In this case, all these compounds are of an industrially usable importance since they can be converted to desired final products by means of known reactions:

$$R'_4Sn + SnCl_4 \rightarrow 2R'_2SnCl_2$$

$$R'_3SnCl + SnCl_4 \rightarrow R'SnCl_3 + R'_2SnCl_2$$

$$SnCl_2 + R'Cl \rightarrow R'SnCl_3$$

If one or several of the aforementioned secondary reactions take place together with the main reaction or overlay the same, variable amounts of tin halide ($SnCl_2$) are formed, which in turn can be recovered alone or used for further reactions.

Processes of the direct synthesis of organotin halides have already been described in numerous patents, in particular using alkyl bromides and iodides as starting halides.

It is known, e.g. from U.S. Pat. No. 3,857,868, that the reaction of the direct synthesis is promoted by the presence of tertiary amines and/or quaternary ammonium salts, it being possible that the latter ones are formed "in situ" from the used tertiary amine and the used alkyl halide.

The reaction is furthermore promoted by the presence of polar solvents and/or catalysts which are capable of reacting with the tin. For this purpose, alcohols, esters or amines are occasionally used. In the direct synthesis of alkyl tin halides, alkyl chlorides have a low reactivity with respect to metallic tin as compared with the corresponding alkyl bromines and iodides. The reaction rate and the yield of desired reaction product increases furthermore with increasing number of the C atoms in the alkyl chain within the alkyl chlorides, it being already difficult to carry out the direct synthesis in the case of the use of $C_4$ alkyl chloride (butyl chloride). The alkyl tin chlorides are therefore produced industrially from tin tetrachloride by means of reaction with trialkyl aluminum compounds, Grignard synthesis or modified Wurtz synthesis, which requires a considerable additional expenditure of costs and process steps.

The present invention is based on the object of making available a process for the direct synthesis of organotin compounds using alkyl chlorides with four or more C atoms, which can be carried out simply and with good yield.

This object is accomplished according to the invention by a process for the type mentioned at the beginning, which is characterized in that the reaction is carried out in the presence of amines of the general formula A) $R^1_aN[(CH_2CH_2O)_mCH_2CH_2OR^2]_{3-a}$ and/or ammonium chlorides of the formula B) $R^1_bN[(CH_2CH_2O)_mCH_2CH_2OR^2]_{4-b}Cl$ wherein a=0, 1 or 2;

b=0, 1, 2 or 3;

$R^1$=linear or branched or cycloaliphatic alkyl having 2 to 24 C atoms, aryl, alkyl aryl or substituted aryl and, if a=2, or b=2 or 3, the $R^1$ groups may be the same or different;

$R^2$=H, linear or branched alkyl having 1 to 20 C atoms, aryl, substituted aryl or alkyl aryl; and m=1-20.

The present invention relates in particular to the direct synthesis of organotin compounds starting from alkyl chlorides, the use of which has been more difficult so far due to their lower reactivity than that of the corresponding bromides and iodides and offers moreover the advantage of the use of less expensive starting substances, namely alkyl chlorides, without it having to be worked under pressure as this is necessary, as a rule, with alkyl halides with less than 4 C atoms in the alkyl part due to their low boiling points.

It became surprisingly apparent according to the invention that the direct synthesis of organotin compounds can be carried out very effectively and efficiently by means of the reaction of metallic tin with alkyl chlorides, if the reaction is carried out in the presence of amines of the aforementioned formula A or ammonium chlorides of the aforementioned formula B. In the case of the use of the amines of the formula A quaternary ammonium salts are formed in situ here.

The reaction is suitably carried out at a temperature between 20° and 200° C., preferably between 140° and 190° C. in the presence of 0.1 to 4 mole of the amine of the formula A and/or of the ammonium chloride of the formula B per gramme atom of tin. The reaction time is suitably 3 to 24 hours, preferably 6 to 10 hours. The reaction is furthermore suitably carried out with 1 to 6 mole, preferably 2 to 3 mole, of alkyl chloride per gramme atom of tin.

Although it is not necessary, the presence of traces of $I_2$ or $Br_2$, in particular in amounts between $10^{-3}$ and 0.2, preferably $10^{-2}$ mole of $I_2$ or $Br_2$ per gramme atom of tin is often advantageous for the reaction. The $I_2$ and/or $BR_2$ can be directly supplied to the reaction or can be added in dissolved fashion and together with the alkyl chloride.

After complete reaction, the amine and/or ammonium chloride can be recovered subsequently by known chemical processes and be used again.

It is important for a good success of the reaction, although it is not imperative, that the alkyl chloride is not present in such a high concentration that it becomes active as a solvent. Therefore the alkyl chloride is preferably slowly added to the reaction drop-wise at the selected reaction temperature so that the selected reaction temperature is maintained. The reaction may be carried out in the presence of suited solvents to keep the reaction mixture sufficiently fluid.

After the reaction, the reaction mixture is customarily filtered to separate non-reacted tin. It can then be washed with acetone and dried and be used again.

The filtrate can be distilled at reduced pressure for recovery of the non-reacted alkyl chloride and/or the possibly used solvent.

In the case of the use of the amine and/or of the ammonium chloride in an amount being equimolar to the tin, mixtures of dialkyl tin dichloride, trialkyl tin chloride and tetraalkyl tin and tin dichloride are formed. In the case of the use of the amine and/or of the ammonium chloride in excess to the equimolar amount trialkyl tin chloride is chiefly obtained and to a variable extent tetralalkyl tin and tin dichloride are additionally obtained. In the case of the use of the amine and/or of the ammonium chloride in catalytic amounts of less than 0.5 mole, in particular 0.1 to 0.33 mole per gramme atom of tin, almost pure dialkyl tin dichloride is obtained and in small variable amounts alkyl tin trichloride is obtained as reaction product.

The organotin compounds produced according to the invention are in particular suited as intermediate products for the production of thermostabilizers, e.g. alkyl tin mercapto compounds, for PVC resins.

The following examples explain the invention.

The ratio of the conversion of the used metallic tin is indicated in %, all types of the tin compound, in which the tin is present in non-metallic fashion, e.g. also possibly present tin dichloride in the reaction product being rated as "usable" product.

The reaction products were analyzed using thin-layer chromatography.

EXAMPLE 1

Tin powder (36 g; 0.3 mole) is suspended at room temperature together with octyl chloride (14.9 g; 0.1 mole) and $I_2$ (0.4 g; $1.57 \times 10^{-3}$ mole) in amine of the average composition $C_{13}H_{27}N[(CH_2CH_2O)_{1.3}CH_2CH_2OH]_2$ (120.3 g; 0.3 mole).

The reaction mixture is heated to 170° to 175° C. under thorough stirring and further octyl chloride (120.1 g; 0.81 mole) is added at this temperature in the course of 6 hours, the said temperature being maintained during the entire feed time. After the addition of the total amount of octyl chloride, the reaction is continued under stirring at 170° to 175° C. for further 3 hours.

After the expiration of this time cooling to 80° to 90° C. is carried out and the non-reacted tin is filtered out, which is then washed with acetone on the filter, dried and weighed. The converted share of the used tin proves to be 84%.

The analysis of the product by means of thin-layer chromatography (TLC) shows as main components $R_3SnCl$ and $R_2SnCl_2$, the first being predominant, and traces of $RSnCl_3$ and $R_4Sn$.

EXAMPLE 2

Tin powder (60 g; 0.5 mole) is suspended together with octyl chloride (14.9 g; 0.1 mole) and $I_2$ (0.635 g; $2.5 \times 10^{-3}$ mole) in amine of the average composition $C_{13}H_{27}N[(CH_2CH_2O)_{1.3}CH_2CH_2OH]_2$ (40.1 g; 0.1 mole). The reaction mixture is heated to 175° C. and further octyl chloride (148.5 g; 1.0 mole) is added at this temperature under thorough stirring in the course of 6 hours.

After the addition, the reaction is continued for 3 hours under stirring at 175° C. Then cooling to 80° to 90° C. is carried out and the non-reacted tin is filtered out, which is washed with acetone on the filter, dried and weighed.

The converted share of the used tin is 65%.

The TLC analysis shows that the product consists mainly of $R_2SnCl_2$ and $RSnCl_3$, predominantly of the first component. A certain amount of $R_3SnCl$ is also present, traces of $R_4Sn$ cannot be detected.

EXAMPLE 3

Tin powder (36 g; 0.3 mole) is suspended together with octyl chloride (178.2 g; 1.2 mole) and $I_2$ (0.76 g; $3 \times 10^{-3}$ mole) in tris-(3,6-dioxaheptyl) amine (194 g; 0.6 mole) and kept at 175° C. under thorough stirring for 12 hours.

At the end of the reaction cooling to 80° to 90° C. is carried out and the non-reacted tin is filtered out, which is washed, dried and weight.

The converted share of the used tin is 78%. The TLC analysis shows that the product consists mainly of $R_3SnCl$ and $R_2SnCl$ with a great predominance of the first component.

EXAMPLE 4

Tin powder (36 g; 0.3 mole) is suspended together with octyl chloride (14.9 g; 0.1 mole) and $I_2$ (0.76 g; $3 \times 10^{-3}$ mole) in diethyl ethoxy ethanol amine (96.75 g; 0.4 mole).

The reaction mixture is heated to 170° to 175° C. under thorough stirring. Further octyl chloride (74.2 g; 0.5 mole) is added at this temperature in the course of 4 hours. After the addition, the reaction is continued under stirring at 175° C. for further 4 hours.

After cooling to 80° to 90° C. the non-reacted tin is filtered out, washed, dried and weighed. The converted share of the used tin is 66.6%.

The TLC analysis shows that the product consists of $R_3SnCl$, $R_4Sn$ and $R_2SnCl_2$ with predominance of the first component.

EXAMPLE 5

Tin powder (24 g; 0.2 mole) is suspended together with octyl chloride (118.8 g; 0.8 mole) and $I_2$ (0.51 g; $2 \times 10^{-3}$ mole) in amine of the average composition $C_{18}H_{37}N[CH_2CH_2O)_{3.5}CH_2CH_2OH]_2$ (66.3 g; 0.1 mole).

The reaction mixture is kept at 160° C. under thorough stirring for 12 hours. After cooling, the non-reacted tin is filtered out, washed, dried and weighed.

The converted share of the used tin is 81.8% and the product consists mainly of $R_3SnCl$, together with $R_2SnCl_2$.

EXAMPLE 6

Tin powder (36 g; 0.3 mole) is suspended together with $I_2$ (0.76 g; $3 \times 10^{-3}$ mole) in amine of the average composition $C_{13}H_{27}N[(CH_2CH_2O)_{1.3}CH_2CH_2OH]_2$. During the course of 8 hours butyl chloride (83.3 g; 0.9 mole) is added dropwise to the reaction mixture heated to 170° to 175° C. by means of a probe reaching under the surface of the reaction mixture in such fashion that the reaction temperature is maintained.

After the expiration of this time the reaction mixture is filtered at 80° C. The non-reacted tin is washed on the filter, dried and weighed.

The converted share of the used tin is 76.4%.

The product consists mainly of $R_3SnCl$.

EXAMPLE 7

Tin powder (36 g; 0.3 mole) is suspended in diethyl ethoxy ethanol amine (24.3 g; 0.15 mole) together with $I_2$ (0.76 g; $3 \times 10^{-3}$ mole). Butyl chloride (83.3 g; 0.9 mole) is added dropwise under stirring in the course of 7.5 hours in the same fashion as explained in example 6. After the addition, the reaction mixture is cooled and the non-reacted tin is filtered out, washed, dried and weighed.

The converted share of the used tin is 64.5%.

The product consists mainly of $R_3SnCl$ together with $R_4Sn$ and $R_2SnCl_2$.

EXAMPLE 8

Tin powder (60 g; 0.5 mole) is suspended in molten ammonium salt diethyl-bis-(ethoxy ethanol) ammonium chloride (71.5 g; 0.25 mole). Heating to 180° C. is carried out and octyl chloride (185.5 g; 1.25 mole) is added dropwise during 5 hours.

After the addition of the total amount of octyl chloride, the reaction is continued at 180° to 185° C. under stirring for further 7 hours.

After the expiration of this time, cooling to 80° to 90° C. is carried out and then the non-reacted tin is filtered out, which is then washed on the filter, dried and weighed.

The converted share of the used tin proves to be 86.5%.

The product consists of $R_3SnCl$ and $R_2SnCl_2$, with slight predominance of the first component.

EXAMPLE 9

Amine of the formula $(C_4H_9)_2N(CH_2CH_2OCH_2CH_2OCH_2CH_2OH)$ (28.8 g; 0.11 mole) is heated to 130° C. together with $I_2$ (0.63 g; $2.5 \times 10^{-3}$ mole).

Tin powder (40 g, 0.34 mole) is suspended at this temperature and dodecyl chloride (143.4 g; 0.7 mole) is added dropwise in the course of 7.5 hours and the temperature is raised up to 180° to 190° C.

The reaction is still continued for further 2.5 hours.

After cooling to 80° to 90° C., the non-reacted tin is filtered out, washed, dried and weighed. The converted share of the used tin is 90%. The product consists mainly of $R_2SnCl_2$ and a small amount of $R_3SnCl$.

We claim:

1. A process for the direct synthesis of organotin compounds of the formula $$R_nSnCl_{4-n}$$

wherein
n=1-4, and
R=a linear or branched or cycloaliphatic alkyl having 4-18 C atoms,
by reacting metallic tin with alkyl chlorides, characterized in that the reaction is carried out in the presence of amines of the general formula
A) $R^1{}_aN[(CH_2CH_2O)_mCH_2CH_2OR^2]_{3-a}$
and/or ammonium chlorides of the formula
B) $R^1{}_bN[(CH_2CH_2O)_mCH_2CH_2OR^2]_{4-b}{}^{Cl}$
wherein
a=0, 1 or 2;
b=0, 1, 2 or 3;
$R^1$=linear or branched or cycloaliphatic alkyl having 2 to 24 C atoms, aryl, alkyl aryl or substituted aryl and, if a=2, or b=2 or 3, the $R^1$ groups may be the same or different;
$R^2$=H, linear or branched alkyl having 1 to 20 C atoms, aryl, substituted aryl or alkyl aryl; and
m=1-20.

2. A process according to claim 1, characterized in that $R^2$ is a linear or branched alkyl having 1 to 4 carbon atoms.

3. A process according to claim 1, characterized in that m is 1-10.

4. A process according to claim 1, characterized in that butyl chloride, octyl chloride or dodecyl chloride is used as alkyl chloride.

5. A process according to claim 1, characterized in that the amine and/or the ammonium chloride is used in a ratio of 0.1 to 0.33 mole per gramme atom of tin.

6. A process according to claim 1, characterized in that equimolar amounts of amine and/or ammonium chloride are used with respect to the tin.

7. A process according to claim 1, characterized in that the amine and/or ammonium chloride are used in excess to the equimolar amount with respect to the tin.

8. A process according to claim 3 characterized in that m is 1-3.

* * * * *